US00PP10081P

United States Patent [19]

Meier et al.

[11] Patent Number: Plant 10,081

[45] Date of Patent: Oct. 21, 1997

[54] 'BA 78-165' KENTUCKY BLUEGRASS

[75] Inventors: Virgil D. Meier, Marysville, Ohio; Jay B. Burr, Salem, Oreg.

[73] Assignee: OMS Investments, Inc., Wilmington, Del.

[21] Appl. No.: 680,168

[22] Filed: Jul. 15, 1996

[51] Int. Cl.[6] ..... A01H 5/00

[52] U.S. Cl. ..... Plt./90.2

[58] Field of Search ..... Plt./90.2

[56] References Cited

U.S. PATENT DOCUMENTS

| | | | |
|---|---|---|---|
| P.P. 3,156 | 5/1972 | Fuchigami et al. | Plt./90.2 |
| P.P. 3,186 | 5/1972 | Barenbrug et al. | Plt./90.2 |
| P.P. 4,336 | 11/1978 | Mayer et al. | Plt./90.2 |
| P.P. 6,280 | 9/1988 | Meier et al. | Plt./90.2 |
| P.P. 6,537 | 1/1989 | Meier et al. | Plt./90.2 |
| P.P. 6,538 | 1/1989 | Meier et al. | Plt./90.2 |
| P.P. 6,585 | 2/1989 | Meier et al. | Plt./90.2 |
| P.P. 7,831 | 3/1992 | Meier et al. | Plt./90.2 |
| P.P. 8,490 | 12/1993 | Meier etal. | Plt./90.2 |
| P.P. 9,036 | 1/1995 | Meier et al. | Plt./90.2 |
| P.P. 9,209 | 7/1995 | Meier et al. | Plt./90.2 |
| P.P. 9,611 | 7/1996 | Meier et al. | Plt./90.2 |
| P.P. 9,848 | 4/1997 | Meier et al. | Plt./90.2 |

*Primary Examiner*—James R. Feyrer

*Attorney, Agent, or Firm*—Jones, Day, Reavis & Pogue

[57] ABSTRACT

A variety of Kentucky Bluegrass having a medium to high level of resistance to leaf spot and melting out disease, red thread and powdery mildew; a moderate tolerance to billbugs; a medium deep green color throughout the growing season; the ability to form a medium to high quality turf under a variety of environmental conditions; a moderately wide leaf blade; a low growth habit; and a high level of seed yielding capacity.

1 Drawing Sheet

BACKGROUND OF THE INVENTION

1. Field of the Invention

The present invention relates to a new and distinct variety of *Poa pretensis* that has been designated Ba 78-165 Kentucky Bluegrass.

2. Description of Related Art

Kentucky bluegrasses have been disclosed in U.S. Plant Pat. No. 3,156, issued May 9, 1972; U.S. Plant Pat. No. 3,186, issued May 23, 1972; U.S. Plant Pat. No. 4,336, issued Nov. 28, 1978; U.S. Plant Pat. No. 6,280, issued Sep. 6, 1988; U.S. Plant Pat. Nos. 6,537 and 6,538, issued on Jan. 17, 1989; U.S. Plant Pat. No. 6,585, issued Feb. 7, 1989, U.S. Plant Pat. No. 7,831, issued Mar. 17, 1992; U.S. Plant Pat. No. 8,490, issued Dec. 7, 1993; U.S. Plant Pat. No. 9,036, issued Jan. 3, 1995; U.S. Plant Pat. No. 9,209, issued Jul. 18, 1995; and pending U.S. Plant patent application Ser. No. 08/453,854, filed May 30, 1995, now U.S. Plant Pat. No. 9,611; Ser. No. 08/532,995, filed Sep. 22, 1995, now U.S. Plant Pat. No. 9,848, and Ser. No. No. 08/604,763, filed Feb. 23, 1996, as well as U.S. Plant patent application Ser. No. 08/680,167, filed coextensively herewith.

SUMMARY OF THE VARIETY

Ba 78-165 plant material originated by crossing Ba 74-157, an unreleased Kentucky Bluegrass plant maintained in the O. M. Scott plant nursery, as the seed parent with Ba 74-501, another unreleased Kentucky Bluegrass plant maintained in the O. M. Scott plant nursery, as the pollen parent. As a result of this breeding, a distinct variety was produced and asexually propagated by rhizomes, tillers and disseminules.

Seed of Ba 78-165 Kentucky Bluegrass was produced first at Marysville, Ohio and later at Gervais, Ore. This seed was used to plant turf performance evaluation trials and later seed production fields.

Asexual production of Ba 78-165 by propagules (tillers and rhizomes) and by disseminules (modified caryopses produced by apomixis) has consistently produced progeny plants indistinguishable from the mother plant. The apomixis level of Ba 78-165 is approximately 96% based upon examining seedling characteristics of approximately 100 to 150 seedlings from different crop years in a growth chamber.

Ba 78-165 has a number of highly desirable characteristics including a medium to high level of resistance to Drechslera spp. that causes leaf spot, melting out and crown rot; a medium to high level of resistance to *Erysiphe graminis* that causes powdery mildew and a medium to high level of resistance to *Laettiseria fuciformis* that causes red thread. Ba 78-165 has an attractive leafy turf type, low growth habit; moderately wide leaf blades and a medium deep green color which can be maintained throughout the entire growing season. Ba 78-165 demonstrates good early spring greening and good winter color under mild winter conditions.

Ba 78-165 is an overall good turfgrass performer as evidenced by medium to high scores for quality and color. Ba 78-165 has a high seed yield potential in the bluegrass seed production region of the northwestern United States.

In comparison with a number of other Kentucky Bluegrass varieties, Ba 78-165 has a significantly longer seed and rachilla than many other Kentucky Bluegrasses and a significantly lower seed count than several other Kentucky Bluegrasses. The panicle of Ba 78-165 Kentucky Bluegrass is significantly shorter than many other Kentucky Bluegrasses, and below average in width, whorl number and branch counts per whorl. Ba 78-165 has, on average, smaller spikelets, glumes and number of florets. The peduncle is above average in length and width. It has a flag leaf that is below average in length, above average in width and thickness relative to most other Kentucky Bluegrasses. The flag leaf ligule is of average length and the leaf margin has significantly fewer hairs than other Kentucky Bluegrasses. The vegetative leaf is above average in length and width and slightly below average in thickness. The ligule of the vegetative leaf is significantly shorter than most other Kentucky Bluegrasses. Ba 78-165 has significantly fewer hairs on the upper ligule margin and collar margin than several of the Kentucky Bluegrass varieties and significantly more hairs than other Kentucky Bluegrasses on the dorsal side of the leaf.

DETAILED DESCRIPTION OF THE VARIETY

Figure 1:
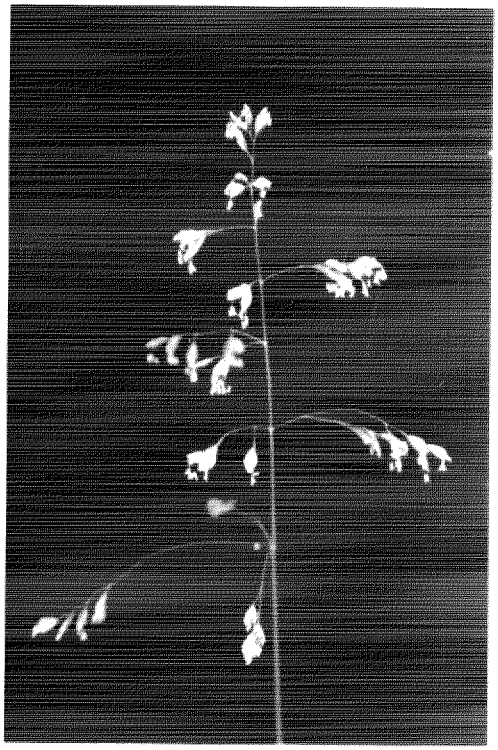
FIG. 1 is a Ba 78-165 Kentucky Bluegrass panicle.
Figure 2:
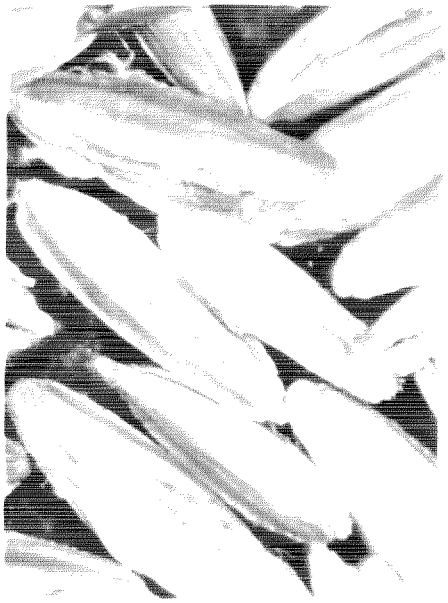
FIG. 2 is a Ba 78-165 Kentucky Bluegrass seed.
Figure 3:
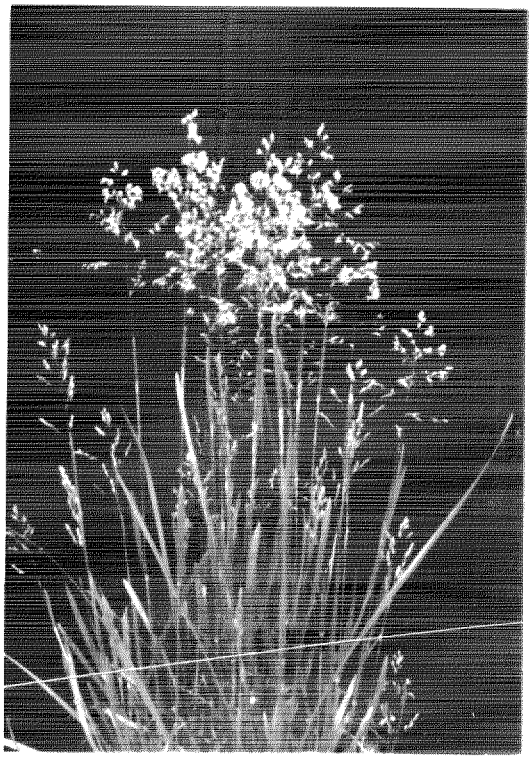
FIG. 3 is a Ba 78-165 Kentucky Bluegrass plant shortly after completing anthesis.

Ba 78-165 Kentucky Bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60°–80° F.), culms are erect averaging 47.5 cm in length and 3.1 nodes per culm. The uppermost internode averages 14.8 cm in length. The peduncle averages 22.4 cm in length and 0.73 mm in width. The vegetative leaf averages 24.2 cm in length, 3.9 mm in width, 0.23 mm in thickness and the ligule 0.35 mm in length. The flag leaf averages 4.0 cm in length, 3.5 mm in width, 0.12 mm in thickness and a ligule length of 1.45 min.

The panicle averages 78.7 mm in length, 48.2 mm in width, and 8.1 whorls. The lowest whorl and the third whorl from the bottom of the panicle average 3.2 and 2.5 branches, respectively. A spikelet in the lowest whorl averages 4.3 mm in length, 2.1 mm in width, 2.8 florets and the outer glume and inner glume average 2.9 and 3.2 mm in length, respectively. A spikelet from the third whorl from the bottom of the particle averages 4.5 mm in length, 2.2 mm in width, 2.9 florets, and the outer glume and inner glume averages 2.7 mm and 3.4 mm in length, respectively.

The conditioned seed of Ba 78-165 averages 3.32 mm in length, 0.97 mm in width, and a rachilla length of 0.50 min. It has a high level of hairs at the base of the lemma, and at the margins of the palea.

Comparisons of Ba 78-165 with other Kentucky Bluegrass varieties in terms of seed numbers per pound are shown in Table 1 as follows:

TABLE 1

Comparison of Seeds Per Pound after Conditioning of Ba 78-165 and Other Kentucky Bluegrass Varieties.

| Variety | Seeds Per Pound |
|---|---|
| Ba78-165 | 965,500 |
| Ba73-366 | 993,500 |
| Ba78-381 | 1,023,250 |
| Abbey | 988,500 |
| Buckingham | 978,000 |
| Coventry | 1,374,750 |
| Garfield | 1,250,500 |
| Merit | 1,250,250 |
| LSD (.50) | 77,042 |

Ba 78-165 differs significantly from several of the other Kentucky Bluegrass varieties in regard to the following morphological characteristics: (1) seed length; (2) rachilla length; (3) panicle length; (4) number of branches in the third whorl; (5) spikelet length in the lowest whorl; (6) glumes in the third whorl; (7) culm length and internode length and color; (8) flag leaf margin hairs; (9) vegetative leaf ligule length, and (10) hairs on the upper margin of the ligule, collar margin and the leaf dorsal side.

Since environmental conditions such as soil and climate may influence morphological characteristics to some extent, comparisons of Ba 78-165 were made with other Kentucky Bluegrass varieties under like conditions and the comparisons are set forth in Tables 2–10 as follows:

TABLE 2

Morphological Comparison of Seed, Rachilla and Lemma and Palea Hairs of Ba 78-165 and Other Kentucky Bluegrass Varieties After Conditioning

| | Seed | | | Hairs* | |
|---|---|---|---|---|---|
| | Length | Width | Rachilla | Lemma | Palea |
| Ba 78-165 | 3.23 | 0.97 | 0.50 | 4.00 | 1.60 |
| Ba 77-700 | 3.20 | 0.85 | 0.77 | 2.80 | 0.90 |
| Abbey | 3.02 | 0.85 | 0.56 | 1.80 | 0.40 |
| Ascot | 3.00 | 0.81 | 0.68 | 6.30 | 1.50 |
| Cannon | 3.32 | 0.85 | 0.72 | 0.20 | 2.00 |
| Gnome | 2.93 | 0.90 | 0.61 | 2.10 | 0.80 |
| Merit | 2.85 | 0.78 | 0.62 | 0.90 | 0.15 |
| Viva | 2.72 | 0.77 | 0.79 | 1.20 | 0.20 |
| LSD (.05) | 0.191 | 0.072 | 0.177 | 1.53 | 0.823 |

*Rating Scale: 0–9; 9 = most hairs

TABLE 3

Morphological Comparison of Panicles, Whorl Number and Whorl Branches of Ba 78-165 and Other Kentucky Bluegrass Varieties in the Greenhouse at Marysville, OH

| | Panicles | | | Number of Branches | |
|---|---|---|---|---|---|
| Variety | Length mm | Width mm | Whorl Number | Lowest Whorl | Third Whorl |
| Ba 78-165 | 78.7 | 48.2 | 8.1 | 3.2 | 2.5 |
| Ba 77-700 | 87.7 | 57.9 | 8.2 | 3.9 | 3.3 |
| Abbey | 86.4 | 54.1 | 9.0 | 4.1 | 3.3 |
| Ascot | 91.4 | 60.7 | 9.1 | 2.4 | 2.3 |
| Cannon | 91.7 | 49.9 | 8.9 | 4.4 | 3.6 |
| Gnome | 85.4 | 43.7 | 9.1 | 3.6 | 3.4 |
| Merit | 77.3 | 38.9 | 8.1 | 2.9 | 2.8 |
| Viva | 82.5 | 46.6 | 8.0 | 3.4 | 3.0 |
| LSD (.05) | 8.03 | 8.83 | 0.65 | 0.71 | 0.59 |

TABLE 4

Morphological Comparison of Spikelets and Florets of Ba 78-165 and Other Kentucky Bluegrass Varieties in the Greenhouse at Marysville, OH

| | Spikelet* | | | | Number of Florets | |
|---|---|---|---|---|---|---|
| | Lowest Whorl | | Third Whorl | | Per Spikelet | |
| Variety | Length mm | Width mm | Length mm | Width mm | Lowest Whorl | Third Whorl |
| Ba 78-165 | 4.3 | 2.1 | 4.5 | 2.2 | 2.8 | 2.9 |
| Ba 77-700 | 4.6 | 2.1 | 4.5 | 2.2 | 2.9 | 3.2 |
| Abbey | 5.0 | 2.3 | 4.9 | 2.3 | 3.3 | 3.3 |
| Ascot | 5.3 | 2.3 | 5.5 | 2.5 | 3.2 | 3.6 |
| Cannon | 4.7 | 2.0 | 4.8 | 2.1 | 3.2 | 3.1 |
| Gnome | 4.5 | 2.3 | 4.7 | 2.2 | 3.2 | 3.0 |
| Merit | 5.0 | 2.5 | 5.2 | 2.5 | 3.9 | 3.8 |
| Viva | 4.9 | 1.9 | 5.0 | 2.0 | 3.3 | 3.3 |
| LSD (.05) | 0.43 | 0.35 | 0.46 | 0.34 | 0.52 | 0.59 |

TABLE 5

Morphological Comparison of Glumes of Ba 78-165 and Other Kentucky Bluegrass Varieties in the Greenhouse at Marysville, OH

| | Glume Length (mm) | | | |
|---|---|---|---|---|
| | Outer | | Inner | |
| Variety | Lowest Whorl | Third Whorl | Lowest Whorl | Third Whorl |
| Ba 78-165 | 2.9 | 2.7 | 3.2 | 3.4 |
| Ba 77-700 | 3.0 | 2.9 | 3.4 | 3.5 |
| Abbey | 2.9 | 3.0 | 3.4 | 3.5 |
| Ascot | 3.9 | 4.0 | 4.3 | 4.5 |
| Cannon | 3.2 | 3.1 | 3.5 | 3.5 |
| Gnome | 2.8 | 2.9 | 3.3 | 3.3 |
| Merit | 3.0 | 3.0 | 3.4 | 3.5 |
| Viva | 3.1 | 3.1 | 3.8 | 3.6 |
| LSD (.05) | 0.29 | 0.29 | 0.29 | 0.28 |

| | Glume Width | | | |
|---|---|---|---|---|
| | Outer | | Inner | |
| Variety | Lowest Outer | Whorl Inner | Third Outer | Whorl Inner |
| Ba 78-165 | 0.6 | 0.5 | 0.6 | 0.6 |
| Ba 77-700 | 0.6 | 0.6 | 0.7 | 0.7 |
| Abbey | 0.6 | 0.7 | 0.9 | 0.8 |
| Ascot | 0.6 | 0.7 | 0.7 | 0.9 |
| Cannon | 0.7 | 0.6 | 0.8 | 0.8 |
| Gnome | 0.6 | 0.6 | 0.8 | 0.8 |
| Merit | 0.6 | 0.6 | 0.8 | 0.9 |
| Viva | 0.5 | 0.5 | 0.7 | 0.7 |
| LSD (.05) | 0.12 | 0.13 | 0.13 | 0.14 |

TABLE 6

Morphological Comparison of Flag Leaves of Ba 78-165 and Other Kentucky Bluegrass Varieties in the Greenhouse at Marysville, OH

| Variety | Length (cm) | Width (mm) | Thickness (mm) | Ligule Length (mm) |
|---|---|---|---|---|
| Ba 78-165 | 4.0 | 3.5 | 0.12 | 1.45 |
| Ba 77-700 | 4.1 | 3.0 | 0.08 | 1.35 |
| Abbey | 4.7 | 3.6 | 0.12 | 1.53 |
| Ascot | 4.4 | 2.9 | 0.11 | 1.52 |
| Cannon | 5.3 | 3.7 | 0.12 | 1.75 |
| Gnome | 4.6 | 3.2 | 0.10 | 1.40 |
| Merit | 4.2 | 2.3 | 0.08 | 0.98 |
| Viva | 3.4 | 2.5 | 0.11 | 1.45 |
| LSD (.05) | 1.14 | 0.61 | 0.02 | 0.24 |

TABLE 7

Morphological Comparison of the Levels of Hairs on the Flag Leaves of Ba 78-165 and Other Kentucky Bluegrass Varieties in the Greenhouse at Marysville, OH

| | Hairs* | | | |
|---|---|---|---|---|
| Variety | Ligule Dorsal | Leaf Margin | Leaf Sheath Margin | Leaf Sheath Dorsal |
| Ba 78-165 | 2.0 | 0.2 | 0.1 | 0.0 |
| Ba 77-700 | 1.3 | 1.8 | 0.8 | 0.0 |
| Abbey | 1.9 | 2.2 | 1.3 | 0.6 |
| Ascot | 0.8 | 1.9 | 0.5 | 1.2 |
| Cannon | 1.4 | 2.4 | 0.8 | 0.0 |
| Gnome | 1.8 | 1.3 | 1.0 | 0.4 |
| Merit | 1.0 | 1.8 | 0.9 | 1.4 |

TABLE 7-continued

Morphological Comparison of the Levels of Hairs on the Flag Leaves of Ba 78-165 and Other Kentucky Bluegrass Varieties in the Greenhouse at Marysville, OH

| | Hairs* | | | |
|---|---|---|---|---|
| Variety | Ligule Dorsal | Leaf Margin | Leaf Sheath Margin | Leaf Sheath Dorsal |
| Viva | 2.5 | 1.5 | 0.4 | 0.0 |
| LSD (.05) | 0.83 | 0.72 | 0.79 | 0.62 |

*Rating Scale: 0–9; 0 = none; 9 = many

TABLE 8

Morphological Comparison of Peduncles, Culms, Number of Nodes per Culm, and Internode Length and Color of Ba 78-165 and Other Kentucky Bluegrass Varieties in the Greenhouse at Marysville, OH

| Variety | Peduncle Length cm | Peduncle Width mm | Culm Length cm |
|---|---|---|---|
| Ba 78-165 | 22.4 | 0.73 | 47.5 |
| Ba 77-700 | 21.6 | 0.68 | 50.6 |
| Abbey | 21.5 | 0.77 | 40.6 |
| Ascot | 17.5 | 0.68 | 41.9 |
| Cannon | 20.0 | 0.74 | 48.3 |
| Gnome | 17.3 | 0.69 | 40.6 |
| Merit | 23.6 | 0.66 | 44.1 |
| Viva | 19.7 | 0.55 | 50.7 |
| LSD (.05) | 2.6 | 0.08 | 2.6 |

| Variety | Number of Nodes Per Culm | Top Internode Length (cm) | Top Internode Color* |
|---|---|---|---|
| Ba 78-165 | 3.1 | 14.8 | 1.9 |
| Ba 77-700 | 3.2 | 14.7 | 0.2 |
| Abbey | 2.6 | 10.7 | 0.1 |
| Ascot | 3.1 | 14.6 | 1.6 |
| Cannon | 3.6 | 13.4 | 0.0 |
| Gnome | 3.2 | 10.6 | 7.2 |
| Merit | 3.0 | 11.8 | 0.8 |
| Viva | 3.5 | 14.9 | 0.0 |
| LSD (.05) | 0.5 | 1.2 | 0.8 |

*Rating Scale; 1–9, 9 = dark purple color

TABLE 9

Morphological Comparison of Vegetative Leaves of Ba 78-165 and Other Kentucky Bluegrass Varieties in the Greenhouse at Marysville, OH

| Variety | Length cm | Width mm | Thickness mm | Length mm |
|---|---|---|---|---|
| Ba 78-165 | 24.2 | 3.9 | 0.23 | 0.35 |
| Ba 77-700 | 23.2 | 3.5 | 0.23 | 0.50 |
| Abbey | 19.3 | 3.5 | 0.21 | 0.45 |
| Ascot | 20.4 | 3.2 | 0.21 | 0.42 |
| Cannon | 24.6 | 3.6 | 0.40 | 0.46 |
| Gnome | 19.5 | 3.8 | 0.24 | 0.48 |
| Merit | 21.8 | 3.6 | 0.23 | 0.41 |
| Viva | 25.0 | 3.2 | 0.24 | 0.40 |
| LSD (.05) | 3.67 | 0.42 | 0.14 | 0.06 |

TABLE 10

Morphological Comparison of the Level of Hair on the Vegetative Leaves of Ba 78-165 and Other Kentucky Bluegrass Varieties in the Greenhouse at Marysville, OH.

| Variety | Leaf Sheath Margin | Leaf Sheath Dorsal | Ligule Upper Margin | Leaf Margin | Collar Margin | Leaf Ventral | Leaf Dorsal |
|---|---|---|---|---|---|---|---|
| Ba 78-165 | 3.3 | 3.9 | 4.5 | 1.3 | 2.0 | 0.2 | 1.7 |
| Ba 77-700 | 3.1 | 5.3 | 7.3 | 1.5 | 2.9 | 0.2 | 0.1 |
| Abbey | 2.1 | 3.3 | 3.9 | 0.4 | 2.9 | 1.0 | 0.2 |
| Ascot | 3.0 | 3.2 | 4.1 | 0.9 | 3.5 | 0.0 | 0.9 |
| Cannon | 3.2 | 3.7 | 6.2 | 0.4 | 2.9 | 0.9 | 0.7 |
| Gnome | 2.9 | 3.1 | 5.6 | 1.0 | 3.9 | 0.9 | 0.5 |
| Merit | 3.7 | 3.0 | 5.4 | 0.1 | 3.2 | 0.5 | 0.0 |
| Viva | 4.3 | 3.9 | 6.6 | 1.5 | 4.5 | 0.2 | 0.2 |
| LSD (.05) | 1.21 | 0.98 | 1.10 | 0.75 | 0.87 | 0.61 | 0.54 |

*Rating Scale: 0–9; 0 = none; 9 = many

Ba 78-165 has performed well throughout the U.S. as exhibited by medium to high turf quality ratings in comparison with other Kentucky Bluegrass varieties. In addition, it has a dark green color which can be maintained throughout the growing season.

With regard to a comparative analysis conducted for purposes of determining color of Ba 78-165 plants relative to other Kentucky Bluegrass varieties, readings were taken of the vegetative color of Ba 78-165 during mid-October while the turf was actively growing with adequate nutrient and water availability. The readings were taken in full sun with several actively growing leaves being compared, one at a time, utilizing color chips from the Munsell Book of Color as a reference. On this basis, the color of Ba 78-165 was determined to be 7.5 GY 4/4. During the same time period, the color of similar leaves of other Kentucky Bluegrass varieties were determined by the same procedure to be as follows: Ascot — 5 GY 4/4; Buckingham — 7.5 GY 4/4; Ba 77-700 — 5 GY 4/6; Midnight — 7.5 GY 4/4; Abbey — 5 GY 4/6; and Victa — 5 GY 4/4. However, it should be noted that the general apparent color of turf does not always correlate directly with the color of the individual actively growing leaves within the turf and that turf color varies with nutrient level and time of year with some varieties being darker or lighter green depending on such factors.

Comparisons of Ba 78-165 with other Kentucky Bluegrass varieties for quality, genetic color, spring greening, summer greenup after dormancy, seedling vigor, density, fall recovery, vertical growth, heat stress, and winter color are set forth hereinafter in Tables 11–25 as follows:

TABLE 11

A Comparison of Quality in Three Test (A–C) of Ba 78-165 and Other Kentucky Bluegrass Varieties Grown in Shade at Marysville, Ohio

| Variety | TEST A | TEST B | TEST C |
|---|---|---|---|
| Ba 78-165 | 3.5 | 2.7 | 2.0 |
| Abbey | 1.8 | 2.0 | 1.5 |
| Banff | 2.9 | 2.1 | 1.6 |
| Bonnieblue | 1.6 | 2.0 | 1.6 |
| Bristol | 3.3 | 2.0 | 1.6 |
| Chateau | 3.5 | 2.0 | 1.5 |
| Coventry | 3.3 | 2.3 | 1.6 |
| Estate | 3.5 | 2.0 | 1.7 |
| Glade | 2.4 | 2.0 | 1.5 |
| Kelly | 1.5 | 1.9 | 1.7 |
| Monopoly | 3.3 | 3.0 | 1.7 |
| Newport | 1.4 | 2.4 | 1.7 |

TABLE 11-continued

A Comparison of Quality in Three Test (A–C) of Ba 78-165 and Other Kentucky Bluegrass Varieties Grown in Shade at Marysville, Ohio

| Variety | TEST A | TEST B | TEST C |
|---|---|---|---|
| Victa | 1.4 | 2.0 | 1.7 |
| LSD (.05) | 0.82 | 0.62 | 0.29 |

Rating Scale: 1–5; 5 = Ideal Turf

TABLE 12

A Comparison of Quality in Three Tests (A–C) of Ba 78-165 and Other Kentucky Bluegrass Varieties at Marysville, OH.

| Variety | TEST A* | TEST B* | TEST C** |
|---|---|---|---|
| Ba 78-165 | 2.2 | 2.6 | 5.0 |
| Allure | 1.3 | 2.4 | 4.3 |
| Adelphi | 1.7 | 2.1 | 5.0 |
| Bonnieblue | 2.0 | 2.5 | 4.0 |
| Bristol | 1.9 | 2.1 | 4.3 |
| Chateau | 1.1 | 2.3 | 4.0 |
| Estate | 1.3 | 2.5 | 4.3 |
| Glade | 1.8 | 2.1 | 3.7 |
| Merit | 2.0 | 2.1 | 3.3 |
| Park | 1.3 | 1.9 | 4.3 |
| Vantage | 1.2 | 2.0 | 4.0 |
| Victa | 1.8 | 2.2 | 5.0 |
| LSD (.05) | 0.39 | 0.30 | 1.67 |

*Rating Scale: 1–5; 5 = Ideal Turf
**Rating Scale: 1–9; 9 = Ideal Turf

TABLE 13

A Comparison of Quality in Three Tests (A–C) of Ba 78-165 and Other Kentucky Bluegrass Varieties ay Marysville, OH.

| Variety | TEST A | TEST B | TEST C |
|---|---|---|---|
| Ba 78-165 | 2.5 | 2.5 | 2.1 |
| Adelphi | 2.3 | 1.8 | 1.8 |
| Bristol | 2.7 | 2.9 | 1.9 |
| Glade | 1.8 | 1.8 | 1.6 |
| Newport | 1.4 | 1.0 | 1.8 |
| Ram I | 2.0 | 2.3 | 2.0 |
| Victa | 2.2 | 1.8 | 1.4 |
| LSD (.05) | 0.95 | 1.23 | 0.42 |

Rating Scale: 1–5; 5 = Ideal Turf

TABLE 14

A Comparison of Quality in Three Tests (A–C) of Ba 78-165 and Other Kentucky Bluegrass Varieties Grown in Shade at Marysville, OH.

| Variety | TEST A | TEST B | TEST C |
|---|---|---|---|
| Ba 78-165 | 6.0 | 7.0 | 7.0 |
| Abbey | 3.0 | 3.0 | 6.0 |
| Adelphi | 6.0 | 5.0 | 7.0 |
| Baron | 4.5 | 4.5 | 5.5 |
| Bristol | 5.5 | 5.5 | 7.5 |
| Chateau | 7.0 | 6.0 | 6.5 |
| Classic | 4.0 | 4.0 | 6.0 |
| Coventry | 5.0 | 4.5 | 6.5 |
| Estate | 6.5 | 5.5 | 6.5 |
| Georgetown | 6.0 | 2.0 | 6.0 |
| Glade | 5.5 | 6.0 | 6.5 |
| Gnome | 4.5 | 4.5 | 5.5 |
| Kelly | 5.0 | 4.0 | 6.0 |
| Kenblue | 5.0 | 6.0 | 5.0 |
| Merion | 4.0 | 5.0 | 7.0 |
| Merit | 4.0 | 4.0 | 5.5 |

TABLE 14-continued

A Comparison of Quality in Three Tests (A–C) of Ba 78-165 and Other Kentucky Bluegrass Varieties Grown in Shade at Marysville, OH.

| Variety | TEST A | TEST B | TEST C |
|---|---|---|---|
| Nassau | 5.5 | 5.0 | 6.0 |
| Ram I | 5.0 | 4.5 | 6.5 |
| Victa | 5.0 | 4.5 | 6.0 |
| LSD (.05) | 2.23 | 3.36 | 1.50 |

Rating Scale: 1–9; 9 = Ideal Turf

TABLE 15

A Comparison of Color of Ba 78-165 and Other Kentucky Bluegrass Varieties Grown in Shade at Marysville, OH

| Variety | Color |
|---|---|
| Ba 78-165 | 7.5 |
| Abbey | 7.0 |
| Adelphi | 7.0 |
| Baron | 7.0 |
| Bristol | 7.0 |
| Chateau | 7.5 |
| Classic | 6.5 |
| Coventry | 7.0 |
| Estate | 7.5 |
| Georgetown | 7.0 |
| Glade | 7.0 |
| Gnome | 7.0 |
| Kelly | 6.5 |
| Kenblue | 7.0 |
| Merion | 7.0 |
| Merit | 7.0 |
| Nassau | 7.0 |
| Ram I | 7.0 |
| Victa | 7.0 |
| LSD (.05) | 0.77 |

Rating Scale: 1–9; 9 = Dark Green

TABLE 16

A Comparison of Color in Two Tests (A–B) of Ba 78-165 and Other Kentucky Bluegrass Varieties at Marysville, Oh.

| Variety | TEST A | TEST B |
|---|---|---|
| Ba 78-165 | 7.3 | 7.3 |
| Abbey | 6.3 | 7.0 |
| Able I | 7.6 | 8.0 |
| Allure | 6.3 | 7.0 |
| Ascot | 8.0 | 7.3 |
| A-34 | 6.0 | 6.3 |
| Banff | 6.7 | 6.3 |
| Baron | 7.0 | 7.3 |
| Bristol | 7.7 | 7.0 |
| Buckingham | 8.0 | 8.0 |
| Cannon | 7.0 | 7.7 |
| Challenger | 7.3 | 6.7 |
| Classic | 6.7 | 6.7 |
| Coventry | 6.3 | 7.0 |
| Eclipse | 7.0 | 8.0 |
| Estate | 6.0 | 7.0 |
| Georgetown | 7.0 | 6.7 |
| Glade | 7.0 | 7.0 |
| Gnome | 7.3 | 7.3 |
| Haga | 7.0 | 6.7 |
| Kelly | 6.7 | 7.0 |
| Kenblue | 7.0 | 7.0 |
| Liberty | 7.0 | 7.3 |
| Merion | 6.7 | 7.0 |
| Merit | 6.3 | 7.0 |
| Midnight | 7.7 | 9.0 |
| Monopoly | 6.0 | 6.0 |

TABLE 16-continued

A Comparison of Color in Two Tests (A–B) of Ba 78-165 and Other Kentucky Bluegrass Varieties at Marysville, Oh.

| Variety | TEST A | TEST B |
|---|---|---|
| Nassau | 8.0 | 7.0 |
| Ram I | 7.3 | 7.0 |
| South Dakota | 7.0 | 7.0 |
| Touchdown | 7.0 | 7.0 |
| Victa | 7.0 | 7.0 |
| Viva | 6.7 | 7.0 |
| LSD (.05) | 0.72 | 0.62 |

Rating Scale: 1–9; 9 = Dark Green

TABLE 17

A Comparison of Color in Two Tests (A–B) of Ba 78-165 and Other Kentucky Bluegrass Varieties at Gervais, OR.

| Variety | TEST A | TEST B |
|---|---|---|
| Ba 78-165 | 6.8 | 7.7 |
| Ba 78-372 | 7.3 | 7.3 |
| Ba 77-700 | 8.0 | 8.0 |
| Abbey | 7.7 | 8.0 |
| Able I | 7.0 | 8.7 |
| A-34 | 6.7 | 6.3 |
| Allure | 7.2 | 7.0 |
| Ascot | 7.5 | 8.0 |
| Baron | 8.0 | 7.3 |
| Banff | 7.0 | 7.0 |
| Bristol | 7.7 | 7.7 |
| Buckingham | 8.0 | 8.7 |
| Cannon | 8.0 | 8.0 |
| Classic | 6.2 | 7.0 |
| Challenger | 6.8 | 7.0 |
| Coventry | 7.5 | 7.0 |
| Eclipse | 6.8 | 7.3 |
| Estate | 7.5 | 7.0 |
| Fairfax | 6.7 | 7.0 |
| Glade | 7.3 | 8.0 |
| Gnome | 8.0 | 7.3 |
| Georgetown | 6.7 | 6.7 |
| Haga | 7.0 | 7.0 |
| Kelly | 7.8 | 7.3 |
| Kenblue | 4.3 | 8.3 |
| Liberty | 7.2 | 7.3 |
| Merion | 6.0 | 6.7 |
| Merit | 7.8 | 7.7 |
| Midnight | 6.2 | 9.0 |
| Monopoly | 7.0 | 6.7 |
| Nassau | 7.7 | 8.0 |
| Ram I | 5.5 | 8.0 |
| South Dakota | 4.3 | 7.7 |
| Touchdown | 7.0 | 6.7 |
| Viva | 7.7 | 7.7 |
| LSD (.05) | 0.74 | 0.69 |

Rating Scale: 1–9; 9 = Dark Green

TABLE 18

A Comparison of Spring Greenup of Ba 78-165 and Other Kentucky Bluegrass Varieties at Marysville, OH.

| Variety | SPRING GREENUP |
|---|---|
| Ba 78-165 | 5.0 |
| Abbey | 3.7 |
| Adelphi | 4.3 |
| Allure | 3.3 |
| Ascot | 5.0 |
| Baron | 4.0 |
| Bristol | 4.7 |

TABLE 18-continued

A Comparison of Spring Greenup of Ba 78-165 and Other Kentucky Bluegrass Varieties at Marysville, OH.

| Variety | SPRING GREENUP |
|---|---|
| Buckingham | 3.7 |
| Chateau | 3.3 |
| Classic | 3.0 |
| Coventry | 3.5 |
| Estate | 3.0 |
| Fairfax | 3.3 |
| Georgetown | 4.0 |
| Glade | 3.0 |
| Gnome | 4.3 |
| Kelly | 3.7 |
| Kenblue | 4.0 |
| Merion | 3.5 |
| Merit | 3.7 |
| Nassau | 3.0 |
| Ram I | 3.3 |
| Victa | 3.7 |
| LSD (.05) | 1.16 |

Rating Scale: 1–9; 9 = Actively Growing

TABLE 19

A Comparison of Summer Greenup of Ba 78-165 and Other Kentucky Bluegrass Varieties after Summer Dormancy Due to Drought and under Low Maintenance at North Brunswick, NJ.

| Variety | Summer Greenup |
|---|---|
| Ba 78-165 | 6.0 |
| Baron | 5.3 |
| Eclipse | 5.7 |
| Georgetown | 3.3 |
| Glade | 6.3 |
| Gnome | 5.0 |
| Haga | 4.0 |
| Kenblue | 5.0 |
| Liberty | 5.7 |
| Merion | 5.3 |
| Merit | 5.3 |
| Midnight | 4.7 |
| Monopoly | 5.3 |
| Nassau | 5.7 |
| Ram I | 5.7 |
| South Dakota | 5.7 |
| LSD (.05) | 1.9 |

Rating Scale: 1–9; 9 = Fastest Greenup after Summer Dormancy

TABLE 20

A Comparison of Winter Color in Two Tests (A–B) of Ba 78-165 and Other Kentucky Bluegrass Varieties under Low Maintenance at North Brunswick, NJ.

| Variety | TEST A | TEST B |
|---|---|---|
| Ba 78-165 | 5.0 | 4.0 |
| Baron | 3.7 | 2.3 |
| Eclipse | 4.3 | 3.3 |
| Georgetown | 6.0 | 6.3 |
| Glade | 4.3 | 1.7 |
| Gnome | 2.7 | 2.0 |
| Haga | 5.3 | 5.0 |
| Kenblue | 3.3 | 1.0 |
| Liberty | 7.0 | 5.7 |
| Merion | 3.0 | 1.7 |
| Merit | 2.7 | 1.7 |
| Midnight | 6.3 | 4.3 |
| Monopoly | 6.7 | 3.3 |

TABLE 20-continued

A Comparison of Winter Color in Two Tests (A–B) of Ba 78-165 and Other Kentucky Bluegrass Varieties under Low Maintenance at North Brunswick, NJ.

| Variety | TEST A | TEST B |
|---|---|---|
| Nassau | 5.3 | 3.0 |
| Ram I | 7.3 | 1.7 |
| South Dakota | 2.0 | 2.7 |
| LSD (.05) | 1.6 | 1.5 |

Rating Scale: 1–9; 9 = Brightest Green Color

TABLE 21

A Comparison of Turf Density in Three Tests (A–C) of Ba 78-165 and Other Kentucky Bluegrass Varieties under Shade Conditions at Marysville, OH.

| Variety | TEST A | TEST B | TEST C |
|---|---|---|---|
| Ba 78-165 | 6.5 | 6.5 | 8.0 |
| Abbey | 3.5 | 6.0 | 7.0 |
| Adelphi | 6.5 | 6.0 | 7.5 |
| Baron | 5.5 | 5.5 | 6.3 |
| Bristol | 5.5 | 6.0 | 8.0 |
| Chateau | 7.0 | 6.0 | 7.0 |
| Classic | 4.0 | 6.0 | 7.0 |
| Coventry | 6.0 | 6.0 | 7.0 |
| Estate | 6.5 | 7.0 | 7.5 |
| Georgetown | 6.0 | 5.0 | 6.0 |
| Glade | 5.5 | 6.5 | 7.5 |
| Gnome | 4.0 | 6.0 | 6.5 |
| Kelly | 4.5 | 6.0 | 7.0 |
| Kenblue | 6.0 | 6.0 | 6.0 |
| Merion | 5.0 | 6.0 | 8.0 |
| Merit | 4.5 | 5.0 | 7.0 |
| Nassau | 6.0 | 5.5 | 6.5 |
| Ram I | 5.5 | 4.5 | 7.0 |
| Victa | 4.5 | 5.5 | 6.5 |
| LSD (.05) | 2.18 | 1.82 | 1.47 |

Rating Scale: 1–9; 9 = maximum density.

TABLE 22

A Comparison of Fall Recovery of Ba 78-165 and Other Kentucky Bluegrass Varieties after Summer Dormancy due to Drought under Low Maintenance at North Brunswick, NJ.

| Variety | FALL RECOVERY |
|---|---|
| Ba 78-165 | 6.0 |
| Baron | 4.0 |
| Eclipse | 6.7 |
| Georgetown | 6.0 |
| Glade | 4.7 |
| Gnome | 3.3 |
| Haga | 4.3 |
| Kenblue | 3.7 |
| Liberty | 6.7 |
| Merion | 4.7 |
| Merit | 5.0 |
| Midnight | 7.7 |
| Monopoly | 5.3 |
| Nassau | 6.3 |
| Ram I | 5.7 |
| South Dakota | 3.3 |
| LSD (.05) | 2.1 |

Rating Scale: 1–9; 9 = Fastest Turf Recovery after Summer Dormancy.

TABLE 23

A Comparison of Seedling Vigor of Ba 78-165 and Other Kentucky Bluegrass Varieties under Low Maintenance at North Brunswick, NJ.

| Variety | SEEDLING VIGOR |
|---|---|
| Ba 78-165 | 7.8 |
| Baron | 8.5 |
| Eclipse | 2.3 |
| Georgetown | 4.3 |
| Glade | 7.8 |
| Gnome | 7.3 |
| Haga | 7.2 |
| Kenblue | 8.2 |
| Liberty | 7.3 |
| Merion | 1.0 |
| Merit | 7.2 |
| Midnight | 5.5 |
| Monopoly | 7.7 |
| Nassau | 6.5 |
| Ram I | 3.3 |
| South Dakota | 7.3 |
| LSD (.05) | 1.3 |

Rating Scale: 1–9; 9 = Best Seedling Vigor

TABLE 24

A Comparison of Vertical Growth of Ba 78-165 and Other Kentucky Bluegrass Varieties under Low Maintenance at North Brunswick, NJ.

| Variety | VERTICAL GROWTH |
|---|---|
| Ba 78-165 | 3.0 |
| Baron | 4.0 |
| Eclipse | 2.7 |
| Georgetown | 5.3 |
| Glade | 3.3 |
| Gnome | 4.0 |
| Haga | 6.7 |
| Kenblue | 8.0 |
| Liberty | 5.7 |
| Merit | 4.0 |
| Midnight | 3.3 |
| Monopoly | 8.0 |
| Nassau | 5.0 |
| Ram I | 3.7 |
| South Dakota | 7.0 |
| LSD (.05) | 1.2 |

Rating Scale: 1–9; 9 = Most Vertical Growth 37 Days after Seeding

TABLE 25

A Comparison of Heat Stress of Ba 78-165 and Other Kentucky Bluegrass Varieties at Marysville, OH.

| Variety | HEAT STRESS |
|---|---|
| Ba 78-165 | 6.0 |
| Abbey | 6.3 |
| Adelphi | 5.7 |
| Allure | 5.3 |
| Ascot | 7.0 |
| Baron | 6.0 |
| Bristol | 6.0 |
| Buckingham | 5.7 |
| Chateau | 6.0 |
| Classic | 5.3 |
| Coventry | 6.0 |
| Estate | 6.0 |
| Fairfax | 6.0 |
| Georgetown | 4.7 |
| Glade | 6.3 |
| Gnome | 6.3 |

TABLE 25-continued

A Comparison of Heat Stress of Ba 78-165 and Other Kentucky Bluegrass Varieties at Marysville, OH.

| Variety | HEAT STRESS |
|---|---|
| Kelly | 6.3 |
| Kenblue | 4.3 |
| Merion | 5.0 |
| Merit | 6.0 |
| Nassau | 6.0 |
| Ram I | 6.0 |
| Victa | 4.0 |
| LSD (.05) | 0.89 |

Rating Scale: 1–9; 9 = Least Heat Stress

Turf diseases are one of the major causes of inconsistent and poor turf performance. Ba 78-165 has been found to have a medium to high level of resistance to the following diseases: (1) leaf spot and melting out caused by *Drechslera poae* (formerly called *Helminthosporium vagans*); (2) powdery mildew caused by *Erysiphe graminis*; and (3) red thread caused by *Laetisaria fuciformis*. Ba 78-165 has displayed tolerance to turf damage due to billbugs.

Comparisons of disease incidence of Ba 78-165 as compared with other Kentucky Bluegrass varieties in regard to leaf spot, rusts, powdery mildew, red thread, and billbugs are presented in Tables 26–31.

TABLE 26

A Comparison of Leaf Spot Incidence in Ba 78-165 and Other Kentucky Bluegrass Varieties at Marysville, OH.

| Variety | LEAF SPOT |
|---|---|
| Ba 78-165 | 35.0 |
| Allure | 66.7 |
| Adelphi | 68.3 |
| Bonnieblue | 73.3 |
| Bristol | 43.3 |
| Chateau | 71.0 |
| Estate | 60.0 |
| Glade | 60.0 |
| Merit | 55.0 |
| Park | 95.0 |
| Vantage | 95.0 |
| Victa | 60.0 |
| LSD (.05) | 26.9 |

Rating Scale: % Disease

TABLE 27

A Comparison of Powdery Mildew Incidence in Two Tests (A–B) of Ba 78-165 and Other Kentucky Bluegrass Varieties Grown in Shade at Marysville, OH.

| Variety | TEST A | TEST B |
|---|---|---|
| Ba 78-165 | 8.0 | 6.5 |
| Abbey | 6.5 | 2.0 |
| Adelphi | 7.0 | 4.5 |
| Baron | 6.0 | 3.0 |
| Bristol | 6.0 | 6.0 |
| Chateau | 6.0 | 4.0 |
| Classic | 6.5 | 3.5 |
| Coventry | 6.0 | 4.6 |
| Estate | 6.5 | 4.5 |
| Georgetown | 6.0 | 4.0 |
| Glade | 7.0 | 5.5 |
| Gnome | 6.5 | 2.5 |
| Kelly | 5.5 | 2.5 |
| Kenblue | 6.0 | 6.0 |

TABLE 27-continued

A Comparison of Powdery Mildew Incidence in Two Tests (A–B) of Ba 78-165 and Other Kentucky Bluegrass Varieties Grown in Shade at Marysville, OH.

| Variety | TEST A | TEST B |
|---|---|---|
| Merion | 5.0 | 2.0 |
| Merit | 5.5 | 3.0 |
| Nassau | 6.0 | 3.5 |
| Ram I | 6.5 | 4.0 |
| Victa | 6.0 | 2.5 |
| LSD (.05) | 1.93 | 2.68 |

TABLE 28

A Comparison of Leaf Spot Incidence in Ba 78-165 and Other Kentucky Bluegrass Varieties under Low Maintenance at North Brunswick, NJ.

| Variety | LEAF SPOT |
|---|---|
| Ba 78-165 | 5.0 |
| Baron | 4.7 |
| Eclipse | 7.0 |
| Georgetown | 4.0 |
| Glade | 3.0 |
| Gnome | 3.7 |
| Haga | 2.7 |
| Kenblue | 1.0 |
| Liberty | 4.7 |
| Merion | 4.3 |
| Merit | 5.7 |
| Midnight | 7.7 |
| Monopoly | 3.3 |
| Nassau | 6.3 |
| Ram I | 4.3 |
| South Dakota | 1.0 |
| LSD (.05) | 1.4 |

Rating Scale: 1–9; 9 = No disease.

TABLE 29

A Comparison of Powdery Mildew Incidence in Two Tests (A–B) of Ba 78-165 and Other Kentucky Bluegrass Varieties Grown in Shade at Marysville, OH.

| Variety | TEST A | TEST B |
|---|---|---|
| Ba 78-165 | 0 | 0 |
| Abbey | 75 | 40 |
| Banff | 45 | 0 |
| Bristol | 30 | 0 |
| Chateau | 50 | 5 |
| Coventry | 15 | 0 |
| Estate | 10 | 0 |
| Glade | 65 | 40 |
| Kelly | 60 | 20 |
| Kenblue | 10 | 0 |
| Monopoly | 5 | 0 |
| Newport | 75 | 25 |
| Victa | 60 | 65 |
| LSD (.05) | 31.3 | 29.1 |

Rating Scale: % Disease

TABLE 30

A Comparison of Red Thread Incidence in Ba 78-165 and Other Kentucky Bluegrass Varieties at Marysville, OH.

| Variety | RED THREAD |
|---|---|
| Ba 78-165 | 8.0 |
| Abbey | 7.7 |
| Ascot | 8.0 |
| Baron | 7.7 |

TABLE 30-continued

A Comparison of Red Thread Incidence in Ba 78-165 and Other Kentucky Bluegrass Varieties at Marysville, OH.

| Variety | RED THREAD |
|---|---|
| Bristol | 7.3 |
| Buckingham | 7.7 |
| Cannon | 8.0 |
| Coventry | 6.3 |
| Fairfax | 8.0 |
| Gnome | 8.0 |
| Haga | 8.0 |
| Kenblue | 4.7 |
| Liberty | 8.0 |
| Merion | 7.7 |
| Merit | 8.0 |
| Midnight | 7.7 |
| Monopoly | 7.7 |
| Park | 6.0 |
| Ram I | 7.3 |
| South Dakota | 7.7 |
| Victa | 8.0 |
| Viva | 7.7 |
| LSD (.05) | 1.14 |

Rating Scale: 1–9; 9 = No disease.

TABLE 31

A Comparison of Billbug Tolerance of Ba 78-165 and Outer Kentucky Bluegrass Varieties at Marysville, OH.

| Variety | BILLBUG TOLERANCE |
|---|---|
| Ba 78-165 | 4.5 |
| Abbey | 4.0 |
| Allure | 1.5 |
| Bristol | 3.3 |
| Challenger | 2.7 |
| Chateau | 1.2 |
| Classic | 3.7 |
| Coventry | 2.3 |
| Eclipse | 3.0 |
| Estate | 2.3 |
| Gnome | 3.7 |
| Kelly | 3.7 |
| Liberty | 3.0 |
| Merit | 3.3 |
| Midnight | 3.7 |
| Nassau | 3.3 |
| Newport | 4.0 |
| Victa | 3.7 |
| Viva | 3.0 |
| LSD (.05) | 1.33 |

Rating Scale: 1–9; 9 = No damage from insect.

Comparisons of Ba 78-165 with other Kentucky Bluegrass varieties for seed head density, plant height, maturity, and seed yields are shown in Table 32–42 as follows:

TABLE 32

A Comparison of Seed Head Density in Mowed Turf of Ba 78-165 and Other Kentucky Bluegrass Varieties at Marysville, OH.

| Variety | SEED HEAD DENSITY |
|---|---|
| Ba 78-165 | 93 |
| Adelphi | 50 |
| Allure | 70 |
| Ascot | 30 |
| Baron | 85 |
| Bristol | 97 |
| Buckingham | 67 |
| Chateau | 63 |

TABLE 32-continued

A Comparison of Seed Head Density in Mowed Turf of Ba 78-165 and Other Kentucky Bluegrass Varieties at Marysville, OH.

| Variety | SEED HEAD DENSITY |
|---|---|
| Classic | 43 |
| Coventry | 40 |
| Estate | 73 |
| Fairfax | 93 |
| Georgetown | 53 |
| Glade | 73 |
| Gnome | 60 |
| Kelly | 80 |
| Kenblue | 7 |
| Merion | 75 |
| Merit | 83 |
| Nassau | 73 |
| Ram I | 77 |
| Victa | 22 |
| LSD (.05) | 25.2 |

Rating Scale: % Seed Head Density.

TABLE 33

A Comparison of Seed Head Density in Mowed Turf of Ba 78-165 and Other Kentucky Bluegrass Varieties at Gervais, OR.

| Variety | SEED HEAD DENSITY |
|---|---|
| Ba 78-165 | 6.0 |
| Ba 76-372 | 6.0 |
| Ba 77-700 | 6.3 |
| Abbey | 6.0 |
| Able I | 7.7 |
| A-34 | 9.0 |
| Allure | 7.7 |
| Ascot | 7.7 |
| Baron | 6.3 |
| Banff | 8.3 |
| Bristol | 5.7 |
| Buckingham | 6.7 |
| Cannon | 6.3 |
| Classic | 8.7 |
| Challenger | 8.0 |
| Coventry | 8.0 |
| Eclipse | 8.6 |
| Estate | 8.0 |
| Fairfax | 8.0 |
| Georgetown | 8.3 |
| Glade | 9.0 |
| Gnome | 7.0 |
| Haga | 8.3 |
| Kelly | 6.7 |
| Kenblue | 9.0 |
| Liberty | 8.3 |
| Merion | 6.3 |
| Merit | 6.0 |
| Midnight | 8.0 |
| Monopoly | 7.7 |
| Nassau | 8.0 |
| Ram I | 8.3 |
| South Dakota | 8.0 |
| Touchdown | 9.0 |
| Viva | 6.3 |
| LSD (.05) | 0.95 |

Rating Scale: 1–9; 9 = No Seed Heads.

TABLE 34

A Comparison of Seed Head Density in Mowed Turf of Ba 78-165 and Other Kentucky Bluegrass Varieties under Low Maintenance at North Brunswick, NJ.

| Variety | SEED HEAD DENSITY |
|---|---|
| Ba 78-165 | 8.3 |
| Baron | 7.0 |
| Eclipse | 1.7 |
| Georgetown | 5.3 |
| Glade | 1.7 |
| Gnome | 6.3 |
| Haga | 5.3 |
| Kenblue | 1.0 |
| Liberty | 6.0 |
| Merion | 6.0 |
| Merit | 8.0 |
| Midnight | 1.0 |
| Monopoly | 4.0 |
| Nassau | 7.0 |
| Ram I | 3.7 |
| South Dakota | 1.3 |
| LSD (.05) | 1.7 |

Rating Scale: 1–9; 9 = Most Seed Heads.

TABLE 35

A Comparison of Plant Height (cm) in Early Spring of Ba 78-165 and Other Kentucky Bluegrass Varities at Gervais, OR.

| Variety | PLANT HEIGHT |
|---|---|
| Ba 78-165 | 17.8 |
| Ba 76-372 | 10.6 |
| Ba 77-700 | 10.9 |
| Abbey | 9.4 |
| Allure | 12.4 |
| Ascot | 8.6 |
| Bristol | 9.6 |
| Buckingham | 8.6 |
| Cannon | 11.7 |
| Chateau | 8.9 |
| Coventry | 6.4 |
| Estate | 8.9 |
| Fairfax | 8.4 |
| Gnome | 7.9 |
| Kelly | 11.4 |
| Newport | 13.7 |
| Victa | 8.1 |
| Viva | 10.2 |
| LSD (.05) | 2.09 |

TABLE 36

A Comparison of Mature Plant Height (cm) in Two Tests (A–B) of Ba 78-165 and Other Kentucky Bluegrass Varieties at Gervais, OR.

| Variety | TEST A | TEST B |
|---|---|---|
| Ba 78-165 | 48.0 | 53.4 |
| Ba 76-372 | 60.5 | 68.4 |
| Ba 77-700 | 49.2 | 60.0 |
| Abbey | 45.0 | 65.0 |
| Allure | 49.2 | 53.0 |
| Ascot | 48.4 | 56.0 |
| Bristol | 62.2 | 69.4 |
| Buckingham | 56.8 | 66.8 |
| Cannon | 50.6 | 68.4 |
| Chateau | 45.6 | 60.2 |
| Coventry | 51.4 | 62.4 |
| Estate | 50.6 | 57.4 |
| Fairfax | 56.4 | 60.6 |
| Gnome | 42.6 | 60.8 |
| Kelly | 48.4 | 65.2 |
| Newport | 61.6 | 74.9 |

TABLE 36-continued

A Comparison of Mature Plant Height (cm) in Two Tests (A–B) of Ba 78-165 and Other Kentucky Bluegrass Varieties at Gervais, OR.

| Variety | TEST A | TEST B |
|---|---|---|
| Victa | 49.8 | 68.2 |
| Viva | 55.0 | 61.6 |
| LSD (.05) | 8.06 | 8.72 |

TABLE 37

A Comparison of Mature Plant Height (cm) in Three Tests (A–C) Conducted in Late June of Ba 78-165 and Other Kentucky Bluegrass Varieties at Gervais, OR.

| Variety | TEST A | TEST B | TEST C |
|---|---|---|---|
| Ba 78-165 | 68.8 | 60.5 | 59.0 |
| Abbey | 65.3 | 60.4 | 50.3 |
| Buckingham | 68.0 | 43.9 | 56.5 |
| Coventry | 60.3 | 42.1 | 51.5 |
| Midnight | 75.0 | 39.2 | 45.0 |
| Vantage | 73.0 | 81.8 | 73.5 |
| LSD (.05) | 7.45 | 4.54 | 7.09 |

TABLE 38

A Comparison of Seed Head Density of Mature Plants of Ba 78-165 and Other Kentucky Bluegrass Varieties at Gervais, OR

| Variety | SEED HEAD DENSITY |
|---|---|
| Ba 78-165 | 8.5 |
| Abbey | 4.0 |
| Buckingham | 6.0 |
| Coventry | 4.5 |
| Midnight | 5.8 |
| Vantage | 7.8 |
| LSD (.05) | 1.25 |

Rating: 1–9; 9 = Most Seed Heads

TABLE 39

A Comparison of Maturity (1%, 50% and 100% Anthesis) in Three Tests (A–C) of Ba 78-165 and Other Kentucky Bluegrass Varieties at Gervais, OR.

| | TEST A | TEST B | | | TEST C | | |
|---|---|---|---|---|---|---|---|
| Variety | 1% | 1% | 50% | 100% | 1% | 50% | 100% |
| Ba 78-165 | 144 | 124 | 126 | 132 | 120 | 133 | 138 |
| Ba 76-372 | 152 | 126 | 129 | 133 | 122 | 132 | 139 |
| Ba 77-700 | 151 | 129 | 134 | 138 | 130 | 137 | 141 |
| Abbey | 150 | 129 | 132 | 137 | 130 | 138 | 141 |
| Allure | 144 | 128 | 131 | 135 | 127 | 136 | 140 |
| Ascot | 140 | 119 | 124 | 132 | 120 | 134 | 140 |
| Bristol | 144 | 125 | 127 | 132 | 122 | 132 | 139 |
| Buckingham | 141 | 123 | 128 | 134 | 117 | 131 | 138 |
| Cannon | 153 | 129 | 132 | 136 | 130 | 138 | 141 |
| Chateau | 144 | 128 | 131 | 135 | 130 | 137 | 140 |
| Coventry | 144 | 127 | 129 | 134 | 130 | 137 | 140 |
| Estate | 143 | 127 | 129 | 135 | 130 | 137 | 140 |
| Fairfax | 144 | 126 | 129 | 133 | 124 | 135 | 139 |
| Gnome | 150 | 129 | 133 | 137 | 130 | 138 | 142 |
| Kelly | 150 | 129 | 133 | 137 | 127 | 137 | 141 |
| Newport | 145 | 120 | 123 | 131 | 119 | 131 | 139 |
| Victa | 151 | 129 | 132 | 136 | 130 | 139 | 143 |
| Viva | 150 | 129 | 133 | 137 | 130 | 138 | 142 |
| LSD (.05) | 2.6 | 2.1 | 2.5 | 1.8 | 5.2 | 3.1 | 2.7 |

Ratings: Days to Reach Percentage Rates of Maturity (1%, 50% or 100%) from Planting Date

TABLE 40

A Comparison of Maturity (1%, 50% and 100% Heading) in Three Tests (A–C) of Ba 78-165 and Other Kentucky Bluegrass Varieties at Gervais, OR.

| | TEST A | | | TEST B | | | TEST C | | |
|---|---|---|---|---|---|---|---|---|---|
| Variety | 1'% | 50% | 100% | 1% | 50% | 100% | 1% | 50% | 100% |
| Ba 78-165 | 105 | 118 | 135 | 100 | 119 | 122 | 120 | 133 | 138 |
| Ba 76-372 | 117 | 139 | 145 | 99 | 120 | 122 | 122 | 132 | 139 |
| Ba 77-700 | 123 | 141 | 146 | 110 | 125 | 127 | 130 | 137 | 141 |
| Abbey | 123 | 139 | 147 | 108 | 124 | 127 | 130 | 138 | 141 |
| Allure | 118 | 134 | 142 | 111 | 125 | 126 | 127 | 136 | 140 |
| Ascot | 106 | 120 | 137 | 88 | 112 | 119 | 120 | 134 | 140 |
| Bristol | 112 | 130 | 140 | 95 | 119 | 122 | 122 | 132 | 139 |
| Buck-ingham | 107 | 124 | 137 | 94 | 112 | 120 | 117 | 131 | 138 |
| Cannon | 124 | 142 | 150 | 113 | 125 | 127 | 130 | 138 | 141 |
| Chateau | 118 | 135 | 142 | 106 | 124 | 126 | 130 | 137 | 140 |
| Cov-entry | 116 | 132 | 142 | 106 | 122 | 125 | 130 | 137 | 140 |
| Estate | 118 | 134 | 142 | 106 | 124 | 126 | 130 | 137 | 140 |
| Fairfax | 114 | 131 | 142 | 103 | 122 | 124 | 124 | 135 | 139 |
| Gnome | 127 | 137 | 148 | 110 | 125 | 127 | 130 | 138 | 142 |
| Kelly | 123 | 135 | 146 | 112 | 125 | 127 | 127 | 137 | 141 |
| New-port | 111 | 124 | 140 | 85 | 110 | 118 | 119 | 131 | 139 |
| Victa | 123 | 139 | 146 | 112 | 125 | 127 | 130 | 139 | 143 |
| Viva | 123 | 140 | 148 | 109 | 125 | 127 | 130 | 138 | 142 |
| LSD (.05) | 5.3 | 4.5 | 3.5 | 5.3 | 4.1 | 1.8 | 5.2 | 3.1 | 2.7 |

Ratings: Days to Reach Percentage Rates of Maturity (1%, 50% or 100%) from Planting Date

TABLE 41

A Comparison of Seed Yields in Four Tests (A–D) of Ba 78-165 and Other Kentucky Bluegrass Varieties at Gervais, OR.

| Variety | TEST A | TEST B | TEST C | TEST D | Mean |
|---|---|---|---|---|---|
| Ba 78-165 | 992 | 1218 | 1197 | 1053 | 1115 |
| Cannon | 970 | 1306 | 558 | 215 | 760 |
| Viva | 920 | 1258 | 521 | 199 | 725 |
| Abbey | 1124 | 1314 | 629 | 319 | 847 |
| Coventry | 786 | 914 | 649 | 352 | 675 |
| Newport | 1165 | 1002 | 1177 | 805 | 1037 |
| LSD (.05) | 209 | 176 | 158 | 140 | |

Ratings: Pounds per Acre.

TABLE 42

A Comparison of Seed Yields in Four Tests (A–D) of Ba 78-165 and Other Kentucky Bluegrass Varieties at Gervais, OR.

| Variety | TEST A | TEST B | TEST C | TEST D |
|---|---|---|---|---|
| Ba 78-165 | 1196 | 982 | 673 | 638 |
| Abbey | 516 | 848 | 483 | 249 |
| Buckingham | 457 | 1071 | 555 | 328 |
| Coventry | 480 | 429 | 111 | 268 |
| Midnight | 112 | 618 | 251 | 233 |
| Vantage | 328 | 663 | 400 | 227 |
| LSD (.05) | 100 | 130 | 81 | 59 |

Ratings: Pounds per Acre.

What is claimed is:

1. A variety of Kentucky Bluegrass plant, substantially as shown and described, characterized by a medium to high level of resistance to a broad spectrum of diseases, including leaf spot and melting out disease, red thread and powdery mildew; a moderate tolerance to billbugs; a medium deep green color throughout the growing season; medium to high quality turf formation under a wide variety of environmental conditions; a moderately wide leaf blade; a low growth habit; and a high level of seed yielding capacity.

* * * * *